US012636500B2

(12) United States Patent
Min et al.

(10) Patent No.: US 12,636,500 B2
(45) Date of Patent: May 26, 2026

(54) NEURAL STIMULATION DEVICE, CONTROL METHOD, AND NEURAL STIMULATION SYSTEM

(71) Applicant: Amygdala Neuro Technologies (ShenZhen) Co., Ltd., Shenzhen (CN)

(72) Inventors: Xiaoyi Min, Shenzhen (CN); Jiangshan Wei, Shenzhen (CN)

(73) Assignee: Amygdala Neuro Technologies (ShenZhen) Co., Ltd., Shenzhen (CN)

( * ) Notice: Subject to any disclaimer, the term of this patent is extended or adjusted under 35 U.S.C. 154(b) by 246 days.

(21) Appl. No.: 18/648,310

(22) Filed: Apr. 26, 2024

(65) Prior Publication Data

US 2024/0278019 A1     Aug. 22, 2024

Related U.S. Application Data

(63) Continuation-in-part of application No. PCT/CN2022/127096, filed on Oct. 24, 2022.

(30) Foreign Application Priority Data

Oct. 29, 2021     (CN) .......................... 202111272446.6

(51) Int. Cl.
    *A61N 1/36*          (2006.01)
    *A61N 1/02*          (2006.01)
(52) U.S. Cl.
    CPC ......... *A61N 1/36139* (2013.01); *A61N 1/025* (2013.01); *A61N 1/36192* (2013.01)
(58) Field of Classification Search
    CPC .............. A61N 1/36192; A61N 1/0551; A61N 1/36031; A61B 5/388
    See application file for complete search history.

(56) References Cited

U.S. PATENT DOCUMENTS 10,569,088 B2 *  2/2020  Dinsmoor .......... A61N 1/36071
2008/0221640 A1  9/2008  Overstreet et al.
(Continued)

FOREIGN PATENT DOCUMENTS

CA          2973855 A1    10/2016
CN       103638599 A     3/2014
(Continued)

OTHER PUBLICATIONS

Carlos J. Anaya, et al., "Evoked Potentials Recorded From the Spinal Cord During Neurostimulation for Pain: A Computational Modeling Study", International Neuromodulation Society, Apr. 10, 2019, 10 pgs.

(Continued)

*Primary Examiner* — Rochelle D Turchen
(74) *Attorney, Agent, or Firm* — USCH Law, PC

(57)          ABSTRACT

A neural stimulation device is disclosed, including: a pulse generator, an evoked compound action potential (ECAP) sensor, and a neural stimulation controller. The neural stimulation controller instructs the ECAP sensor to sense an ECAP after a pulse is generated by the pulse generator within a first pulse generation cycle, adjust an amplitude of a pulse generated within a second pulse generation cycle in response to a peak-to-peak value of the ECAP being not in a comfort range, and adjust, according to an expected peak-to-peak value, an amplitude of a pulse generated within a third pulse generation cycle in response to a peak-to-peak value of the ECAP after the pulse is generated within the second pulse generation cycle being still not in the comfort range. The expected peak-to-peak value is in the comfort range including an amplitude dimension of the pulse and a peak-to-peak value dimension of the ECAP.

20 Claims, 4 Drawing Sheets

(56) References Cited

U.S. PATENT DOCUMENTS

| | | | |
|---|---|---|---|
| 2008/0300655 A1 | 12/2008 | Cholette | |
| 2016/0157769 A1* | 6/2016 | Min | G16H 50/50 |
| | | | 600/547 |
| 2016/0158550 A1 | 6/2016 | Hou et al. | |
| 2018/0126169 A1 | 5/2018 | Hou et al. | |
| 2019/0099602 A1 | 4/2019 | Esteller et al. | |
| 2019/0366094 A1 | 12/2019 | Esteller et al. | |
| 2020/0316382 A1 | 10/2020 | Esteller | |
| 2021/0121700 A1 | 4/2021 | Dinsmoor et al. | |
| 2021/0187299 A1 | 6/2021 | Dinsmoor et al. | |
| 2021/0386991 A1 | 12/2021 | Bourget et al. | |

FOREIGN PATENT DOCUMENTS

| | | | |
|---|---|---|---|
| CN | 106039564 A | 10/2016 | |
| CN | 109965870 A | 7/2019 | |
| CN | 110072590 A | 7/2019 | |
| CN | 112351813 A | 2/2021 | |
| CN | 112351814 A | 2/2021 | |
| CN | 112843488 A | 5/2021 | |
| CN | 113226449 A | 8/2021 | |
| CN | 113967319 A | 1/2022 | |
| CN | 114404800 A | 4/2022 | |
| EP | 4424359 A1 | 9/2024 | |
| SU | 982702 A1 | 12/1982 | |
| WO | 2012151449 A1 | 11/2012 | |
| WO | 2019190710 A1 | 10/2019 | |
| WO | 2019246579 A1 | 12/2019 | |
| WO | 2021146778 A1 | 7/2021 | |

OTHER PUBLICATIONS

Fei, JI, et al., "Advances in electrically evoked compound action potential testing in cochlear implants", Chinese Journal of Otology, vol. 9, No. 2, Jun. 16, 2011, 5 pgs.

Amygdala Neuro Technologies (ShenZhen) Co., Ltd., International Search Report with English translation, PCT/CN2022/140842, Feb. 15, 2023, 5 pgs.

Amygdala Neuro Technologies (ShenZhen) Co., Ltd., CN First Office Action, CN 2021115826207, Jul. 4, 2022, 15 pgs.

Amygdala Neuro Technologies (ShenZhen) Co., Ltd., Notification to Grant Patent Right for Invention, CN 2021115826207, Sep. 6, 2022, 6 pgs.

Amygdala Neuro Technologies (ShenZhen) Co., Ltd., European Search Report, EP22885877.5, Jan. 3, 2025, 8 pgs.

Amygdala Neuro Technologies (ShenZhen) Co., Ltd., European Search Report, EP22910105.0, Feb. 4, 2025, 8 pgs.

* cited by examiner 303                    301

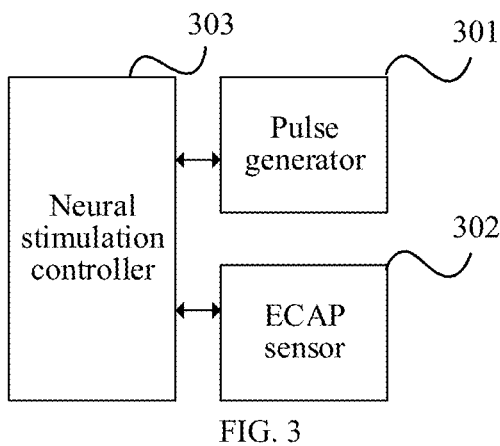

Obtain a peak-to-peak value
of an ECAP

402

Detect whether
the peak-to-peak value of the
ECAP is in a comfort range

Yes

No

403

Detect
whether the
peak-to-peak value of the
ECAP is greater than a peak-
to-peak value
upper limit Yes

404

Adjust an amplitude of a pulse
generated within a second pulse
generation cycle to a product
obtained by multiplying a preset
down-adjustment coefficient by
an amplitude of a pulse generated
within a first pulse sending cycle No

405

Adjust an amplitude of a pulse
generated within a second pulse
generation cycle to a weighted
average, obtained according to a
preset up-adjustment coefficient,
of pulse amplitude upper and
lower limits in the comfort range

FIG. 4

NEURAL STIMULATION DEVICE, CONTROL METHOD, AND NEURAL STIMULATION SYSTEM

CROSS-REFERENCE TO RELATED APPLICATION

The present disclosure is a continuation in part of PCT Patent Application No. PCT/CN2022/127096, filed Oct. 24, 2022, which claims priority to Chinese Patent Application No. 202111272446.6 filed on Oct. 29, 2021, each of which is incorporated to the present disclosure by reference in its entirety.

TECHNICAL FIELD

Embodiments of the present disclosure relate to the field of medical instruments, and in particular, to a neural stimulation device, a control method, and a neural stimulation system.

BACKGROUND

With the progress and development of medical technology, a technology of controlling and treating diseases by sending nerve pulses has been gradually matured. An evoked compound action potential (ECAP) is a sum of all action potentials caused by electrical stimulation applied to fibers. Clinical studies have shown a wealth of scientific evidences to support the implementation, based on feedback control of the ECAP, of a closed-loop spinal cord electrical stimulation (SCS) system for the treatment of chronic pains. For example, characterization of the influence of an amplitude of spinal cord stimulation on dorsal column fiber activation through related parameters of the ECAP, founded by John Parker, has been widely studied. John Parker's study shows that there is a function relationship between a peak-to-peak value of the ECAP and an amplitude of a stimulation current, and the peak-to-peak value of the ECAP will increase linearly as the stimulation current increases after reaching a threshold. Besides, the ECAP is related to sensations of patients on stimulation pulses, and a higher ECAP may cause the patients to have stronger stimulation sensations. Recent clinical work further indicates that a stimulation frequency has an impact on the amplitude of the ECAP and perceived stimulation sensations of patients who are treated for chronic back and/or leg pain with the SCS system.

In an existing SCS system, a numerical value of an ECAP caused by a stimulation pulse in the spinal cord is recorded after the stimulation pulse occurs, and the recorded ECAP value is compared with a desired target or set value. Then, an output of a next stimulation is automatically adjusted according to a comparison result, so as to ensure a constant ECAP intensity. Such an adjustment requires multiple comparisons of the ECAP value and the target value to adjust the amplitude of the pulse so as to continuously approach the target value. This makes the patients have to endure discomfort for a long time, and it also consumes more power, with a low efficiency in adjusting the stimulation pulse.

SUMMARY

Some embodiments of the present disclosure provide a neural stimulation device, including: a pulse generator, an evoked compound action potential (ECAP) sensor, and a neural stimulation controller, where the neural stimulation controller is configured to: instruct the ECAP sensor to sense the evoked compound action potential after a first pulse is generated by the pulse generator within a first pulse generation cycle, adjust an amplitude of a second pulse generated by the pulse generator within a second pulse generation cycle in response to a first peak-to-peak value of the evoked compound action potential that is sensed being not in a comfort range, and adjust, according to an expected peak-to-peak value, an amplitude of a third pulse generated by the pulse generator within a third pulse generation cycle in response to a second peak-to-peak value of the evoked compound action potential that is sensed after the second pulse is generated by the pulse generator within the second pulse generation cycle being still not in the comfort range; where the expected peak-to-peak value is in the comfort range, and the comfort range includes an amplitude dimension of the pulse and a peak-to-peak value dimension of the evoked compound action potential.

Some embodiments of the present disclosure further provide a neural stimulation system, including: the neural stimulation device described above and an electrode lead electrically connected to the neural stimulation device.

Some embodiments of the present disclosure further provide a control method applied at a neural stimulation device, including: applied at a neural stimulation device, where the neural stimulation device includes a neural stimulation controller, a pulse generator and an evoked compound action potential (ECAP) sensor, and where the neural stimulation controller is configured to: instruct the ECAP sensor to sense an evoked compound action potential after a first pulse is generated by the pulse generator within a first pulse generation cycle; and adjust an amplitude of a second pulse generated by the pulse generator within a second pulse generation cycle in response to a first peak-to-peak value of the evoked compound action potential that is sensed being not in a comfort range, and adjust, according to an expected peak-to-peak value, an amplitude of a third pulse generated by the pulse generator within a third pulse generation cycle in response to a second peak-to-peak value of the evoked compound action potential that is sensed after the pulse is generated by the pulse generator within the second pulse generation cycle being still not in the comfort range; where the expected peak-to-peak value is in the comfort range, and the comfort range includes an amplitude dimension of the pulse and a peak-to-peak value dimension of the evoked compound action potential.

BRIEF DESCRIPTION OF THE DRAWINGS

One or more embodiments are illustrated exemplarily with reference to the accompanying drawings, and these exemplary descriptions do not constitute a limitation on the embodiments. Elements having the same reference numeral in the accompanying drawings indicate similar elements, and the figures in the accompanying drawings do not constitute a scale limitation, unless otherwise stated.

FIG. 3 is a schematic structural diagram of a neural stimulation device according to an embodiment of the present disclosure.

FIG. 4 is a flowchart of pulse adjustment according to an embodiment of the present disclosure.

DETAILED DESCRIPTION OF THE EMBODIMENTS

Figure 1:
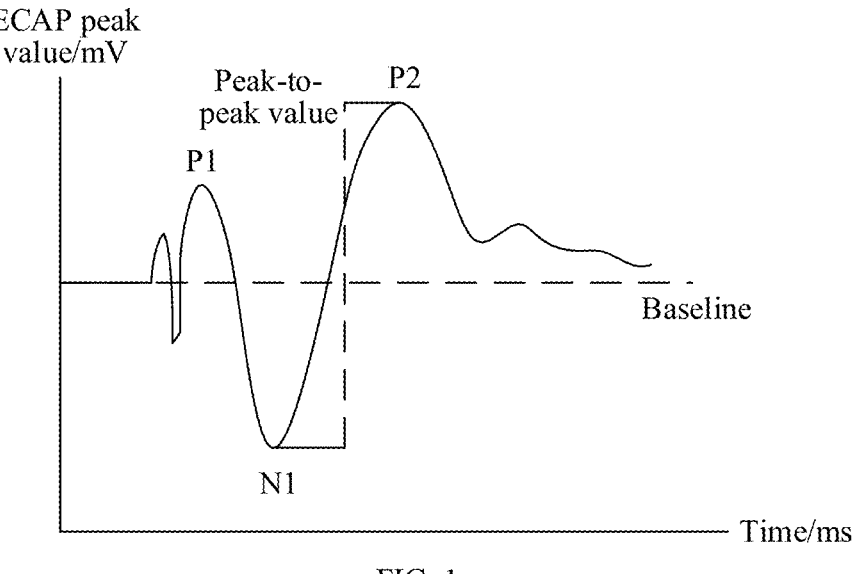
FIG. 1 is a schematic diagram of a waveform of an ECAP sensed at an ECAP sensing window in the existing technology.

As is seen from the Background, when the conventional electrical stimulation device, after acting on a human body, adjusts and outputs a stimulation pulse according to a preset ECAP size and a sensed ECAP result, the efficiency of adjusting the stimulation pulse is low, and a patient cannot be treated effectively in a timely manner. Therefore, how to provide a neural stimulation device that can timely, accurately, and automatically adjust the stimulation pulse to an appropriate state is an urgent problem that needs to be solved.

Embodiments of the present disclosure provide a neural stimulation device, including: a pulse generator, an ECAP sensor, and a neural stimulation controller. The pulse generator is configured to generate a pulse according to an instruction from the neural stimulation controller. The ECAP sensor is configured to sense an evoked compound action potential according to an instruction from the neural stimulation controller. The neural stimulation controller is configured to: instruct the ECAP sensor to sense the evoked compound action potential after a pulse is generated within a first pulse generation cycle, adjust an amplitude of a pulse generated within a second pulse generation cycle in response to a peak-to-peak value of the evoked compound action potential that is sensed being not in a comfort range, and adjust, according to an expected peak-to-peak value, an amplitude of a pulse generated within a third pulse generation cycle in response to a peak-to-peak value of the evoked compound action potential that is sensed after the pulse is generated within the second pulse generation cycle being still not in the comfort range. The expected peak-to-peak value is in the comfort range, and the comfort range includes an amplitude dimension of the pulse and a peak-to-peak value dimension of the evoked compound action potential.

The neural stimulation device provided in the embodiments of the present disclosure senses the evoked compound action potential after the pulse is generated within the first pulse generation cycle. In response to the peak-to-peak value of the sensed evoked compound action potential being not in the comfort range, an amplitude of a pulse to be generated within a next pulse generation cycle (i.e., the second pulse generation cycle) is immediately adjusted. In addition, after the pulse is generated within the second pulse generation cycle, the peak-to-peak value of the evoked compound action potential is obtained. In response to the peak-to-peak value being still not in the comfort range, an amplitude of a pulse to be generated within a further next pulse generation cycle (i.e., the third pulse generation cycle) is adjusted according to the expected peak-to-peak value in the comfort range, so that the peak-to-peak value of the third pulse generation cycle is in the comfort range. When the peakto-peak value of the evoked compound action potential is not in the comfort range, the amplitude of the pulse applied to the patient can be efficiently and easily adjusted through only two steps, ensuring that the peak-to-peak value of the evoked compound action potential caused by the adjusted pulse can accurately fall into the comfort range. This enables the neural stimulation device to automatically provide an effective pulse therapy to the patient in a timely manner according to changes in the physical condition of the patient, to avoid discomfort of the patient and even injury to the patient due to an improper pulse.

To make the objectives, technical solutions, and advantages of embodiments of the present disclosure clearer, the following will describe the various embodiments of the present disclosure in detail with reference to the accompanying drawings. Those of ordinary skill in the art can understand that in the various embodiments of the present disclosure, many technical details are set forth in order to enable readers to better understand the present disclosure. However, the technical solutions claimed by the present disclosure can also be implemented even without these technical details and the various changes and modifications based on the following embodiments. The division of the following embodiments is for convenience of description and should not constitute any limitation on the specific implementations of the present disclosure. The various embodiments can be combined and referenced to each other without conflicts.

The following will provide specific descriptions of the implementation details of the neural stimulation device in the present disclosure in conjunction with specific embodiments. The following content is only for the convenience of understanding the provided implementation details and is not necessary for implementing the present disclosure.

FIG. 1 is a schematic diagram of a waveform of an ECAP curve sensed at an ECAP sensing window. It is seen from FIG. 1 that after a blank period, the ECAP curve has a plurality of peaks and valleys, such as peak P1, peak P2, and valley N1. The valley with the smallest peak value is valley N1 (i.e., a valley with the largest absolute value below a baseline is valley N1), and the peak with the largest peak value on the right of valley N1 is peak P2. A difference value between the maximum peak value P2 and the minimum peak value N1 of the ECAP curve is used to represent a peak-to-peak value of an ECAP, i.e., the black dashed line in FIG. 1.

Figure 2:
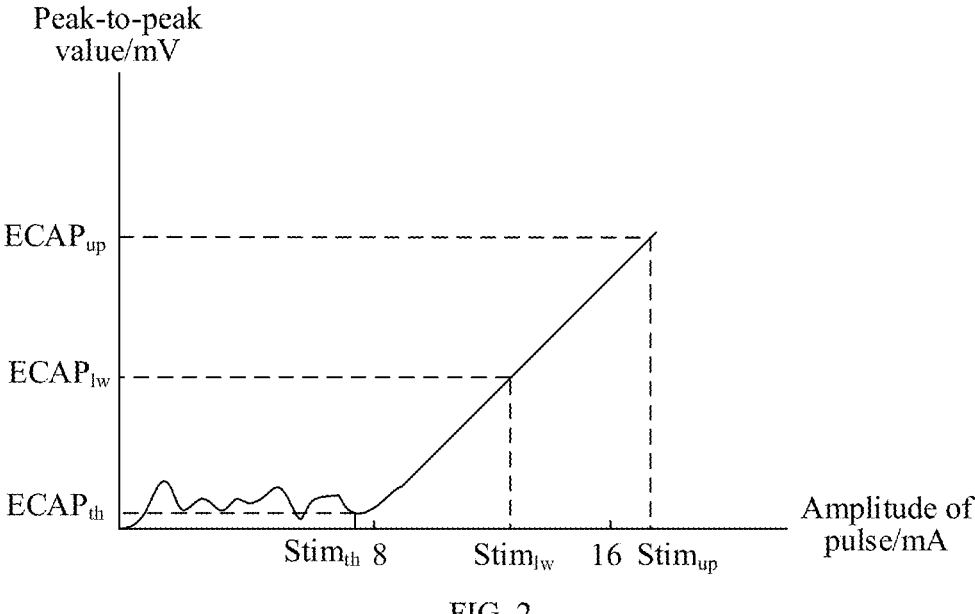
FIG. 2 is a schematic diagram of a relationship between a peak-to-peak value of an ECAP and an amplitude of a pulse when a patient receives electrical stimulation treatment in the existing technology.

John Parker's study indicates that the peak-to-peak value of the ECAP is considered to be in a function relationship with an amplitude of a stimulation pulse, and the ECAP is related to a comfort level of a patient. FIG. 2 is a schematic diagram of a relationship between a peak-to-peak value of an ECAP and an amplitude of a pulse when a patient receives electrical stimulation treatment. Through the schematic diagram, it is found that the peak-to-peak value of the ECAP increases linearly as an amplitude of a stimulation current increases after the peak-to-peak value of the ECAP reaches an activation threshold. Meanwhile, the patient usually begins to feel changes in the intensity of the stimulation pulse only after the peak-to-peak value exceeds a sensing threshold $ECAP_{th}$, and a difference between the sensing threshold $ECAP_{th}$ and the activation threshold of the peak-to-peak value of the ECAP is relatively small. According to data in FIG. 2, the peak-to-peak value reaches the sensing threshold $ECAP_{th}$ when the amplitude $Stim_{th}$ of the stimulation pulse is 7.8 mA. The patient feels that the stimulation enters a comfortable level when the amplitude $Stim_{lw}$ of the stimulation pulse is 12.8 mA. The patient begins to feel an excessively strong stimulation and begins to feel uncomfortable when the amplitude $Stim_{up}$ of the stimulation pulse is 17 mA. Therefore, the patient has a comfortable amplitude range for the stimulation pulse, and this amplitude range corresponds linearly to a range of the peak-to-peak value of the ECAP.

Based on the above understanding, a first aspect of the embodiments of the present disclosure provides a neural stimulation device that can be applied in various stimulation pulse therapies, such as a spinal cord stimulation (SCS) system, a dorsal root ganglion stimulation (DRG) system, etc. This embodiment takes the application in a spinal cord stimulation scenario as an example for explanation.

As shown in FIG. 3, the neural stimulation device provided in the first aspect of the embodiments of the present disclosure includes a pulse generator 301, an ECAP sensor 302, and a neural stimulation controller 303.

The pulse generator 301 is configured to generate a pulse according to an instruction from the neural stimulation controller 303.

The selection of the pulse generator 301 in the actual application has a plurality of options, including a circuit for generating stimulation pulses and a corresponding circuit board including a plurality of electrical components. Generally, the circuit for generating stimulation pulses includes a boosting circuit, an energy storage component, and a switching circuit. In one example, the boosting circuit may be selected from a circuit including a boost IC chip, a charge pump (switched capacitor converter), or an inductive DC-DC converter. In one example, the energy storage component is a capacitor. In one example, the switching circuit is a circuit including an NMOS switch. A specific selection of the pulse generator in this embodiment is not limited.

The ECAP sensor 302 is configured to sense an evoked compound action potential according to an instruction from the neural stimulation controller 303.

The selection of the ECAP sensor 302 in the actual application has a plurality of options, including a sensing circuit. The sensing circuit includes a filter and related circuits, an amplifier and related circuits, and analog-to-digital conversion circuits. In some embodiments, the sensing circuit further includes a comparator to determine whether a valid signal is perceived, and a specific selection of the ECAP sensor in this embodiment is not limited.

The neural stimulation controller 303 is configured to: instruct the ECAP sensor 302 to sense the evoked compound action potential after a pulse is generated within a first pulse generation cycle, adjust an amplitude of a pulse generated within a second pulse generation cycle in response to a peak-to-peak value of the evoked compound action potential that is sensed being not in a comfort range, and adjust, according to an expected peak-to-peak value, an amplitude of a pulse generated within a third pulse generation cycle in response to a peak-to-peak value of the evoked compound action potential that is sensed after the pulse is generated within the second pulse generation cycle being still not in the comfort range. The expected peak-to-peak value is in the comfort range, and the comfort range includes an amplitude dimension of the pulse and a peak-to-peak value dimension of the evoked compound action potential.

There are multiple options for the neural stimulation controller in practical applications, including any or a combination of a logic circuit, a microcontroller unit (MCU), a central processing unit (CPU), a microprocessor, a programmable logic controller (PLC), a field programmable gate array (FPGA), a programmable array logic (PAL), a generic array logic (GAL), and a complex programmable logic device (CPLD). This embodiment does not limit the specific selection of the neural stimulation controller.

In the embodiment, "comfort range" refers to a numerical range of related parameters of the neural stimulation device and a numerical range of corresponding body stress parameters when a pulse generated by the neural stimulation device makes a patient feel comfortable. For example, the related parameters of the neural stimulation device include an amplitude of a pulse and the like. The corresponding body stress parameters include a peak-to-peak value of an ECAP and the like. In an embodiment, the amplitude dimension of the pulse in the comfort range is manifested as including a minimum amplitude of the pulse in the comfort range, a maximum amplitude of the pulse in the comfort range, and the like. The peak-to-peak value dimension in the comfort range is manifested as including a minimum peak-to-peak value of an ECAP corresponding to the pulse with the minimum amplitude in the comfort range, a maximum peak-to-peak value of an ECAP corresponding to the pulse with the maximum amplitude in the comfort range, and the like. The amplitude dimension of the pulse in the comfort range can also be manifested as including not only the minimum amplitude of the pulse in the comfort range and the maximum amplitude of the pulse in the comfort range, but also one or more of all amplitudes between the minimum amplitude of the pulse in the comfort range and the maximum amplitude of the pulse in the comfort range. The peak-to-peak value dimension in the comfort range can also be manifested as including not only the minimum peak-to-peak value of the ECAP corresponding to the pulse with the minimum amplitude in the comfort range and the maximum peak-to-peak value of the ECAP corresponding to the pulse with the maximum amplitude in the comfort range, but also one or more of peak-to-peak values of ECAPs corresponding to multiple pulses with amplitudes between the minimum amplitude of the pulse in the comfort range and the maximum amplitude of the pulse in the comfort range. One or more comfort ranges may be provided. For example, each pulse frequency and/or body posture corresponds to a respective comfort range. The comfort range may also include other dimensions. In an example, the comfort range also includes dimensions such as a body posture, a pulse frequency, etc. That is, different pulse frequencies and/or body postures and corresponding comfort ranges are integrated into unified information. The comfort range may be generated by a doctor during patients' visiting and follow-up, or generated by a patient through a corresponding application program. The comfort range may be stored in the neural stimulation controller or in a storage component that is communicatively connected with the neural stimulation controller.

This embodiment has no specific limitations on the specific manifestation of the comfort range. The comfort range may be manifested and stored in any form among a multi-dimensional array, a curve, a chart, a queue, a heap, a stack, a vector, a chain table, a tree, or a hash table that contain the aforementioned data.

"The expected peak-to-peak value is in the comfort range" means that the expected peak-to-peak value is any value in a value range formed by the minimum peak-to-peak value in the comfort range and the maximum peak-to-peak value in the comfort range. Whether the peak-to-peak value is in the comfort range means whether the peak-to-peak value is in the value range formed by the minimum peak-to-peak value in the comfort range and the maximum peak-to-peak value in the comfort range.

The parameters stored in the neural stimulation device further include a sensing threshold and an amplitude of a pulse corresponding to the sensing threshold. Similarly, the sensing threshold and the amplitude of the pulse corresponding to the sensing threshold may be stored in the neural stimulation controller or in the storage component that is communicatively connected with the neural stimulation controller.

In some embodiments, the parameters stored in the neural stimulation device include all values of the related parameters of the neural stimulation device which can be modified by the neural stimulation device and the corresponding body stress parameters. For example, all the values of the related parameters of the neural stimulation device include amplitudes of several pulses adopted when the pulse generator generates the pulses. The body stress parameters include peak-to-peak values of corresponding ECAPs. The curve of the peak-to-peak value of the ECAP and the amplitude of the pulse shown in FIG. 2 is one of the manifestations, which may also be manifested and stored in any form among a multidimensional array, a chart, a queue, a heap, a stack, a vector, a chain table, a tree, or a hash table.

When the neural stimulation device used for spinal cord stimulation starts to operate after being implanted into the body of the patient, the neural stimulation controller instructs, according to various pre-stored or set related parameters of pulse generating and evoked compound action potential sensing, the pulse generator to periodically generate pulses with specific amplitudes to the patient at a certain generating frequency. Furthermore, after the pulse generator starts to generate the pulses to the patient, the neural stimulation controller instructs the ECAP sensor to start the sensing of the evoked compound action potential to sense responses (i.e., the evoked compound action potential) of the patient after the patient receives the pulses. Initial pulses are set and generated according to pulse parameters that are set by the doctor during the implantation of the neural stimulation device or in a follow-up visit. The pulses generated by the neural stimulation device implanted into the body of the patient may make the patient in a comfortable state. Then, the existing pulses may possibly make the patient no longer in the comfortable state due to the influence of factors such as a physical condition of the patient or an external environment. In this case, the neural stimulation controller needs to adjust the pulse according to the peak-to-peak value of the sensed ECAP.

In some embodiments, after the generating of a pulse within a pulse generation cycle is completed, the neural stimulation controller instructs the ECAP sensor to sense the ECAP caused by the pulse generated within a current pulse generation cycle, acquires ECAP information of the current pulse generation cycle through the ECAP sensor, such as the maximum value (the value of peak P2) and the minimum value (the value of valley N1) of the ECAP in the current pulse generation cycle, and then obtains the peak-to-peak value of the ECAP in the current pulse generation cycle. Then, the neural stimulation controller determines whether the peak-to-peak value of the ECAP in the current pulse generation cycle is in the comfort range. When the peak-to-peak value of the ECAP in the current pulse generation cycle is not in the comfort range, the neural stimulation controller adjusts an amplitude of a pulse generated within a next pulse generation cycle. For ease of understanding, the current pulse generation cycle is taken as a first pulse generation cycle, and subsequent two pulse generation cycles are taken as a second pulse generation cycle and a third pulse generation cycle in sequence, respectively. In response to the peak-to-peak value of the ECAP sensed within the first pulse generation cycle being not in the comfort range, the neural stimulation controller adjusts an amplitude of a pulse generated within the second pulse generation cycle and acquires, through the ECAP sensor, ECAP information caused by the generating of the second pulse after the second pulse is generated. In response to the peak-to-peak value of the ECAP sensed within the second pulse generation cycle being still not in the comfort range, the neural stimulation controller obtains the expected peak-to-peak value of the ECAP. The expected peak-to-peak value is in the comfort range, so as to ensure that the patient feels comfortable in the stimulation caused by the pulse. The neural stimulation controller then sets, according to the expected peak-to-peak value, an amplitude of a pulse generated within the third pulse generation cycle, so as to ensure that the pulse received by the patient can make the patient in the comfortable state. The comfort range includes the amplitude dimension of the pulse and the peak-to-peak value dimension of the evoked compound action potential.

In some embodiments, in response to the peak-to-peak value of the evoked compound action potential sensed within the first pulse generation cycle being not in the comfort range, the neural stimulation controller detects a relationship between the peak-to-peak value and a peak-to-peak value upper limit in the comfort range and a relationship between the peak-to-peak value and a peak-to-peak value lower limit in the comfort range. In response to the peak-to-peak value being greater than the peak-to-peak value upper limit, the neural stimulation controller adjusts the amplitude of the pulse generated within the second pulse generation cycle to a product obtained by multiplying a preset down-adjustment coefficient by the amplitude of the pulse generated within the first pulse generation cycle. In response to the peak-to-peak value being less than the peak-to-peak value lower limit, the neural stimulation controller adjusts the amplitude of the pulse generated within the second pulse generation cycle to a weighted average, obtained according to a preset up-adjustment coefficient, of pulse amplitude upper and lower limits in the comfort range. FIG. 4 is a flowchart of adjusting the amplitude of the pulse generated within the second pulse generation cycle according to the peak-to-peak value of the ECAP sensed within the first pulse generation cycle. As shown in FIG. 4, the adjustment process includes the following operations. At operation 401, a peak-to-peak value of an ECAP is obtained. That is, the neural stimulation controller instructs the ECAP sensor to sense an evoked compound action potential caused by a first pulse within a first pulse generation cycle, and obtains the peak-to-peak value of the ECAP within the first pulse generation cycle. At operation 402, whether the peak-to-peak value of the ECAP is in the comfort range is detected. That is, the neural stimulation controller detects whether the peak-to-peak value of the ECAP within the first pulse generation cycle is in the comfort range. In response to the peak-to-peak value of the ECAP within the first pulse generation cycle being in the comfort range, operation 401 is executed to obtain a peak-to-peak value of an ECAP within a next pulse generation cycle. In response to the peak-to-peak value of the ECAP within the first pulse generation cycle being not in the comfort range, operation 403 is executed, i.e., detecting whether the peak-to-peak value of the ECAP is greater than the peak-to-peak value upper limit. In response to the peak-to-peak value of the ECAP being greater than the peak-to-peak value upper limit in the comfort range, operation 404 is executed, i.e., adjusting the amplitude of the pulse generated within the second pulse generation cycle to a product obtained by multiplying a preset down-adjustment coefficient by the amplitude of the pulse generated within the first pulse generation cycle. In response to the peak-to-peak value of the ECAP being not greater than the peak-to-peak value upper limit in the comfort range, operation 405 is executed, i.e., adjusting the amplitude of the pulse generated within the second pulse generation cycle to a weighted average, obtained according to a preset up-adjustment coefficient, of pulse amplitude upper and lower limits in the comfort range.

For example, after acquiring the peak-to-peak value of the ECAP within the current pulse generation cycle and the comfort range and determining that the peak-to-peak value of the ECAP is not in the comfort range, the neural stimulation controller determines that the amplitude of the pulse generated within the current pulse generation cycle is extremely large and an amplitude of a subsequently generated pulse needs to be decreased in response to the peak-to-peak value of the ECAP sensed within the current pulse generation cycle being greater than the peak-to-peak value upper limit in the comfort range. The neural stimulation controller obtains, according to the preset down-adjustment coefficient and the amplitude of the pulse generated within the current pulse generation cycle, the amplitude of the pulse generated within the next pulse generation cycle. That is, the neural stimulation controller sets the amplitude of the pulse generated within the next pulse generation cycle to the product obtained by multiplying the down-adjustment coefficient by the amplitude of the pulse generated within the current pulse generation cycle, so that the amplitude of the pulse generated within the next pulse generation cycle decreases to a certain extent. For example, if the amplitude of the pulse generated within the current pulse generation cycle is $stim_1$, and the peak-to-peak value of the ECAP sensed within the current pulse generation cycle is greater than the peak-to-peak value upper limit of the ECAP in the comfort range, the amplitude of the pulse generated within the next pulse generation cycle is $stim_2 = stim_1 \times \alpha$, where $\alpha$ is the down-adjustment coefficient.

In response to the peak-to-peak value of the ECAP sensed within the current pulse generation cycle being less than the peak-to-peak value lower limit in the comfort range, the neural stimulation controller determines that the amplitude of the pulse generated within the current pulse generation cycle is extremely small and an amplitude of a subsequently generated pulse needs to be increased. The neural stimulation controller obtains, according to the preset up-adjustment coefficient and the pulse amplitude upper and lower limits in the comfort range, the amplitude of the pulse generated within the next pulse generation cycle. That is, the neural stimulation controller adjusts the amplitude of the pulse generated within the next pulse generation cycle to the weighted average, obtained according to the preset up-adjustment coefficient, of the pulse amplitude upper and lower limits in the comfort range, so that the amplitude of the pulse generated within the next pulse generation cycle increases to a certain extent. For example, if the peak-to-peak value of the ECAP sensed within the current pulse generation cycle is less than the peak-to-peak value lower limit of the ECAP in the comfort range, the amplitude of the pulse generated within the next pulse generation cycle is $stim_2 = stim_{up} \times \beta + stim_{lw} \times (1-\beta)$, where $stim_{up}$ and $stim_{lw}$ are the pulse amplitude upper and lower limits in the comfort range, respectively, and $\beta$ is the up-adjustment coefficient.

After adjusting the amplitude of the pulse generated within the next pulse generation cycle, the neural stimulation controller instructs, within the next pulse generation cycle, the pulse that has been subjected to amplitude adjustment to be generated, and instructs the ECAP sensor to sense an ECAP caused by the new pulse to obtain a peak-to-peak value of the ECAP. In response to the peak-to-peak value of the sensed ECAP being in the comfort range, the amplitude of the pulse is no longer adjusted. In response to the peak-to-peak value of the sensed ECAP being still not in the comfort range, the neural stimulation controller further adjusts an amplitude of a pulse generated within a further next pulse generation cycle. The amplitude of the pulse generated within the next pulse generation cycle is directly adjusted according to the up-adjustment or down-adjustment coefficient, so that the peak-to-peak value of the ECAP falls into the comfort range as soon as possible, greatly simplifying the amplitude adjustment steps and improving the efficiency and accuracy of pulse adjustment.

Each of the up-adjustment coefficient and the down-adjustment coefficient acquired by the neural stimulation controller is in a range of 0.4 to 0.6, e.g., 0.5. The peak-to-peak value of the ECAP caused by the pulse of which the amplitude has been adjusted by the setting of the appropriate up-adjustment coefficient and down-adjustment coefficient can fall into the comfort range as soon as possible, and an injury to the patient due to excessive adjustment performed on the amplitude of the pulse is avoided.

Figure 5:
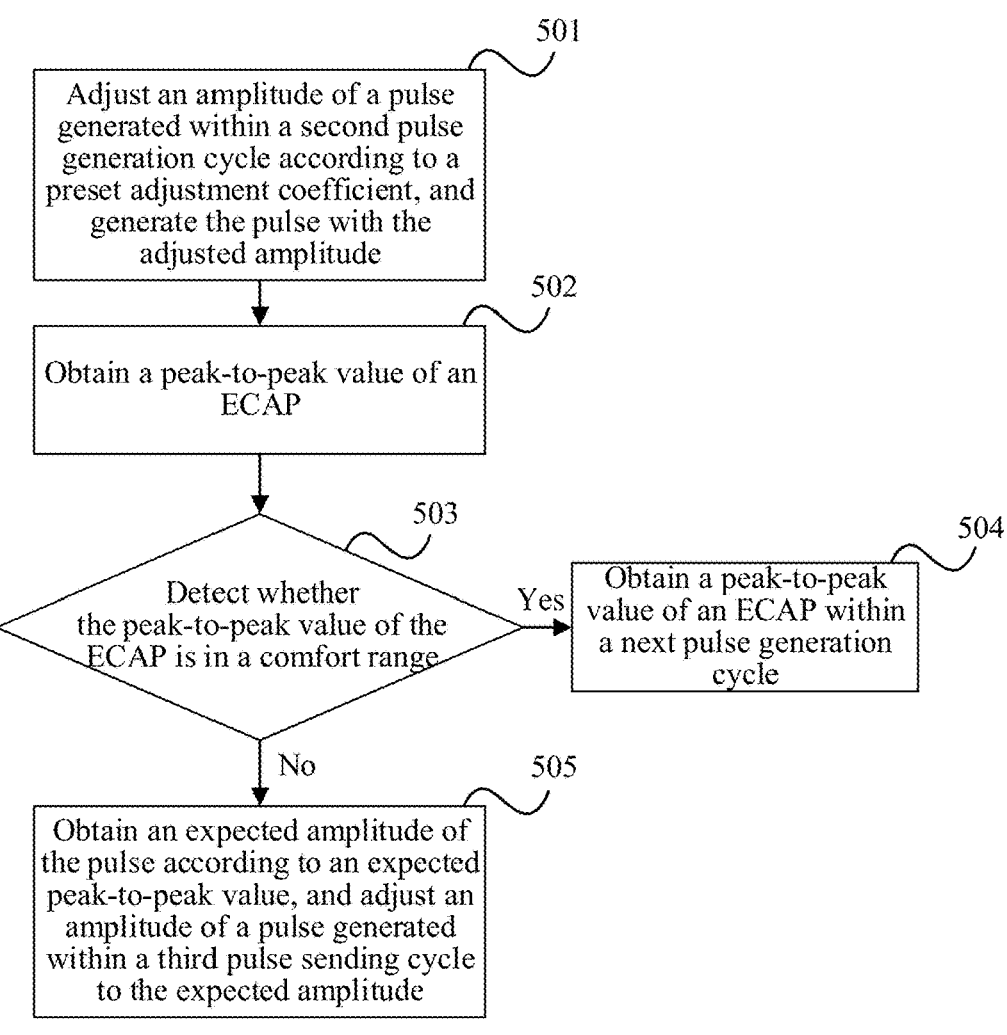
FIG. 5 is another flowchart of pulse adjustment according to an embodiment of the present disclosure.

In another example, the neural stimulation controller is configured to: in response to the peak-to-peak value of the evoked compound action potential sensed after the pulse is generated within the second pulse generation cycle being still not in the comfort range, obtain an expected peak-to-peak value according to the peak-to-peak value upper and lower limits of the evoked compound action potential in the comfort range and an expectation coefficient, obtain an expected amplitude of the pulse according to the expected peak-to-peak value and a transformation coefficient, and use the expected amplitude as an amplitude of a pulse generated within the third pulse generation cycle. FIG. 5 is a flowchart of adjusting an amplitude of a pulse generated within a third pulse generation cycle according to a peak-to-peak value of an ECAP sensed within a second pulse generation cycle. As shown in FIG. 5, the adjustment process includes the following operations. At operation 501, an amplitude of a pulse generated within a second pulse generation cycle is adjusted according to a preset adjustment coefficient, and the pulse with the adjusted amplitude is generated. That is, the neural stimulation controller sets, according to a relationship between the peak-to-peak value of the ECAP sensed within the first pulse generation cycle and the peak-to-peak value upper limit in the comfort range and a relationship between the peak-to-peak value of the ECAP sensed within the first pulse generation cycle and the peak-to-peak value lower limit in the comfort range, the amplitude of the pulse generated within the second pulse generation cycle to be the product obtained by multiplying the amplitude of the pulse generated within the first pulse generation cycle by the down-adjustment coefficient or the weighted average, obtained according to the preset up-adjustment coefficient, of pulse amplitude upper and lower limits in the comfort range, and instructs the pulse generator to generate the pulse with the adjusted amplitude. At operation 502, a peak-to-peak value of an ECAP is obtained. That is, the neural stimulation controller instructs, after instructing the pulse with the adjusted amplitude to be generated, sensing the ECAP caused by the pulse with the adjusted amplitude to obtain the peak-to-peak value of the ECAP. At operation 503, whether the peak-to-peak value of the ECAP is in the comfort range is detected. In response to detecting that the peak-to-peak value of the ECAP is in the comfort range, operation 504 is executed, i.e., acquiring a peak-to-peak value of an ECAP within a next pulse generation cycle. In response to detecting that the peak-to-peak value of the ECAP is not in the comfort range, operation 505 is executed, i.e., obtaining an expected amplitude of the pulse according to an expected peak-to-peak value, and adjusting an amplitude of a pulse generated within a third pulse generation cycle to the expected amplitude.

Figure 6:
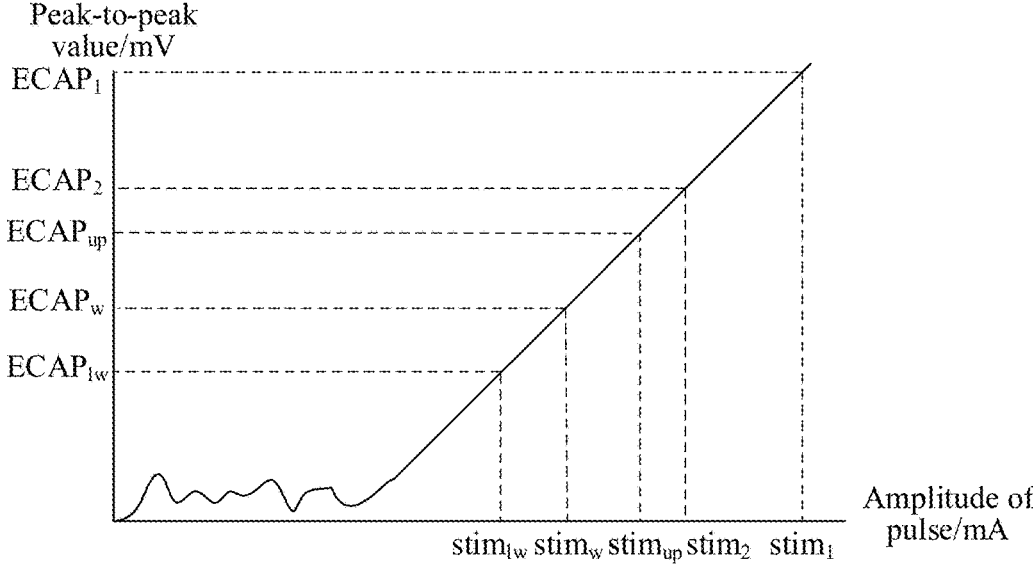
FIG. 6 is a schematic diagram of changes in an amplitude of a pulse and a peak-to-peak value of an ECAP according to an embodiment of the present disclosure.

For example, in response to the peak-to-peak value of the ECAP caused by the pulse generated within the second pulse generation cycle after amplitude adjustment being still not in the comfort range, the neural stimulation controller obtains the expected peak-to-peak value of the ECAP according to the peak-to-peak value upper and lower limits of the ECAP in the comfort range and the expectation coefficient. For example, the weighted average of the peak-to-peak value upper and lower limits in the comfort range is obtained according to the expectation coefficient. The weighted average is used as the expected peak-to-peak value, i.e., the expected peak-to-peak value is $ECAP_w = ECAP_{up} \times \delta + ECAP_{lw} \times (1-\delta)$, where $ECAP_{up}$ is the peak-to-peak value upper limit in the comfort range, $ECAP_{lw}$ is the peak-to-peak value lower limit in the comfort range, and $\delta$ is the expectation coefficient. In an example of pulse adjustment, changes in the amplitude of the pulse and the peak-to-peak value of the ECAP are as shown in FIG. 6. The amplitude of the pulse generated within the first pulse generation cycle is $stim_1$, and the peak-to-peak value of the ECAP caused thereby is $ECAP_1$. The amplitude of the pulse generated within the second pulse generation cycle is $stim_2$, and the peak-to-peak value of the ECAP caused thereby is $ECAP_2$. The peak-to-peak value upper limit in the comfort range is $ECAP_{up}$, and the peak-to-peak value lower limit in the comfort range is $ECAP_{lw}$. The pulse amplitude upper limit is $stim_{up}$, and the pulse amplitude lower limit is $stim_{lw}$. During the pulse adjustment, the peak-to-peak value $ECAP_1$ of the ECAP sensed within the first pulse generation cycle is greater than the peak-to-peak value upper limit of the ECAP in the comfort range. The neural stimulation controller adjusts, according to the preset down-adjustment coefficient, the amplitude of the pulse generated within the next pulse generation cycle from $stim_1$ to $stim_2$. After the pulse with the adjusted amplitude is generated, the peak-to-peak value $ECAP_2$ of the ECAP sensed within the second pulse generation cycle is still greater than the peak-to-peak value upper limit $ECAP_{up}$ in the comfort range. In this case, the neural stimulation controller calculates the expected peak-to-peak value $ECAP_w$ according to the peak-to-peak value upper limit $ECAP_{up}$ and the peak-to-peak value lower limit $ECAP_{lw}$ in the comfort range and the expectation coefficient, and adjusts, according to the expected peak-to-peak value $ECAP_w$, the amplitude of the pulse generated within the next pulse generation cycle to the expected amplitude $stim_w$.

Further, the expectation coefficient is in a range of 0.4 to 0.6, e.g., 0.5. By the selection of the appropriate value range, the expected peak-to-peak value can accurately fall into the comfort range.

After acquiring the expected peak-to-peak value $ECAP_w$, the neural stimulation controller obtains the expected amplitude of the pulse corresponding to the expected peak-to-peak value $ECAP_w$ in combination with the transformation coefficient between the peak-to-peak value of the ECAP and the amplitude of the pulse, and uses the expected amplitude as the amplitude of the pulse generated within the third pulse generation cycle. Since the expected peak-to-peak value is accurately obtained according to the peak-to-peak value upper and lower limits in the comfort range and the expectation coefficient, the expected amplitude of the pulse obtained according to the transformation coefficient can make the patient in the comfortable state, thereby accurately adjusting the pulse.

In some embodiments, the transformation coefficient is a ratio of a difference between the peak-to-peak value upper and lower limits in the comfort range to a difference between the pulse amplitude upper and lower limits in the comfort range, or the transformation coefficient is a ratio of a difference between the peak-to-peak values of the evoked compound action potentials within the first pulse generation cycle and the second pulse generation cycle to a difference between the amplitudes of the pulses respectively generated within the first pulse generation cycle and the second pulse generation cycle. That is, the transformation coefficient is $R = (ECAP_{up} - ECAP_{lw})/(stim_{up} - stim_{lw})$, or the transformation coefficient is $R = (ECAP_1 - ECAP_2)/(stim_1 - stim_2)$.

When acquiring the transformation coefficient between the expected peak-to-peak value of the evoked compound action potential and the expected amplitude of the pulse, the neural stimulation controller may directly read the transformation coefficient calculated according to the ratio of the difference between the peak-to-peak value upper and lower limits of the ECAP in the comfort range to the difference between the pulse amplitude upper and lower limits in the comfort range from a storage component or obtain the transformation coefficient through communication. Or, the neural stimulation controller may calculate a desired transformation coefficient according to the ratio of the difference between the peak-to-peak values within the first pulse generation cycle and the second pulse generation cycle to the difference between the amplitudes of the pulses respectively generated within the first pulse generation cycle and the second pulse generation cycle. The expected amplitude is obtained through the transformation coefficient and the expected peak-to-peak value by using a linear relationship between the peak-to-peak value of the evoked compound action potential and the amplitude of a corresponding pulse. The neural stimulation controller can accurately and efficiently adjust the peak-to-peak value within the third pulse generation cycle to be in the comfort range.

In some embodiments, the neural stimulation controller is configured to calculate the expected amplitude of the pulse according to the following formula.

$$S_t = S_C - \frac{E_C - E_t}{R}$$

Where $S_t$ is the expected amplitude of the pulse, $S_C$ is the amplitude of the pulse generated within the first pulse generation cycle, $E_C$ is the peak-to-peak value of the ECAP sensed within the first pulse generation cycle, $E_t$ is the expected peak-to-peak value, and R is the transformation coefficient.

Or, the expected amplitude of the pulse is calculated according to the following formula.

$$S_t = S'_C - \frac{E'_C - E_t}{R}$$

Where $S_t$ is the expected amplitude of the pulse, $S'_C$ is the amplitude of the pulse generated within the second pulse generation cycle, $E'_C$ is the peak-to-peak value of the ECAP sensed within the second pulse generation cycle, $E_t$ is the expected peak-to-peak value, and R is the transformation coefficient.

The neural stimulation controller may calculate the expected amplitude according to the amplitude of the pulse generated within the first pulse generation cycle and the peak-to-peak value of the sensed ECAP in combination with the expected peak-to-peak value and the transformation coefficient. Or, the neural stimulation controller may calculate the expected amplitude according to the amplitude of the pulse generated within the second pulse generation cycle and the peak-to-peak value of the sensed ECAP in combination with the expected peak-to-peak value and the transformation coefficient. This ensures that the expected amplitude can be accurately calculated, and the calculated expected amplitude can fall to the middle of an amplitude range of the pulse in the comfort range as soon as possible, to avoid such a situation that an actual peak-to-peak value falls beyond the comfort range after pulse generating due to a deviation between theory and practice, thereby ensuring the accuracy and validity of pulse adjustment.

In some embodiments, the neural stimulation controller is further configured to obtain different comfort ranges according to different body postures and/or different frequencies of pulses. The comfort ranges are different if the patient is in different postures or subjected to stimulation pulses with different frequencies. After acquiring ECAP information of a pulse generation cycle, the neural stimulation controller obtains different comfort ranges, according to a frequency of a pulse generated within the current pulse generation cycle and/or a body posture of the patient within the current pulse generation cycle, for comparing to the peak-to-peak value of the ECAP. Different comfort ranges are provided according to the frequency of the pulse and/or the body posture and are compared with the peak-to-peak value of the ECAP, so that the feeling of the patient is accurately determined to ensure the accuracy of stimulation pulse adjustment. In the process that the neural stimulation controller adjusts the amplitude of the pulse to make the peak-to-peak value of the ECAP in the comfort range, the neural stimulation controller stops the current adjustment process and re-determines whether the peak-to-peak value of the ECAP is in a new comfort range in response to the comfort range changing due to the frequency of the pulse or the body posture, and the neural stimulation controller starts new adjustment in response to the peak-to-peak value being not in the new comfort range.

Figure 7:
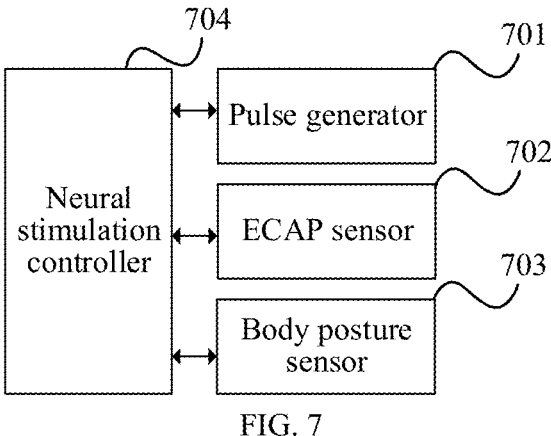
FIG. 7 is another schematic structural diagram of a neural stimulation device according to an embodiment of the present disclosure.

The neural stimulation device further includes: a body posture sensor. The body posture sensor is communicatively connected to the neural stimulation controller and is configured to sense a current body posture. The neural stimulation controller is further configured to obtain the body posture through the body posture sensor to obtain a comfort range corresponding to the body posture. Referring to FIG. 7, the neural stimulation device includes a pulse generator 701, an ECAP sensor 702, a body posture sensor 703, and a neural stimulation controller 704. The neural stimulation controller is communicatively connected to the other components. When the neural stimulation device enters a working state, the neural stimulation controller obtains a current body posture of a patient according to body posture data sensed by the body posture sensor. Before determining whether the peak-to-peak value of the sensed ECAP is in the comfort range, the neural stimulation controller calls the corresponding comfort range according to the body posture or the frequency of the pulse generated within the current pulse generation cycle in combination with the body posture, then compares the peak-to-peak value of the sensed ECAP with the comfort range, and determines whether to adjust an amplitude of a subsequent pulse according to a comparison result. The body posture sensor is added to sense the body posture, and a specific comfort range is accurately obtained according to the body posture, thereby accurately determining whether the patient is in the comfortable state to ensure the accuracy of pulse adjustment.

The selection of the body posture sensor in the actual application has a plurality of options, including any one or any combination of a position sensor, attitude sensor, displacement sensor, and acceleration sensor as well as related circuits, and a specific selection of the body posture sensor in this embodiment is not limited.

In another embodiment, in response to the peak-to-peak value of the ECAP sensed within the first pulse generation cycle being not in the comfort range, the neural stimulation controller is further configured to detect whether the peak-to-peak value of the ECAP sensed within the first pulse generation cycle is less than a sensing threshold $ECAP_{th}$. In response to the peak-to-peak value of the ECAP sensed within the first pulse generation cycle being less than the sensing threshold $ECAP_{th}$, similar to the above embodiment, the amplitude of the pulse generated within the second pulse generation cycle is adjusted. Unlike the above embodiment, the amplitude $stim_2$ of the pulse generated within the next pulse generation cycle (i.e., the second pulse generation cycle) is calculated according to the following formula.

$$stim_2 = stim_1 + stim_{lw} - stim_{th} + \gamma \times (stim_{up} - stim_{lw})$$

Where $stim_{up}$ and $stim_{lw}$ are the pulse amplitude upper and lower limits in the comfort range, respectively, $stim_{th}$ is an amplitude of a pulse corresponding to the sensing threshold $ECAP_{th}$, $stim_1$ is the amplitude of the pulse generated within the first pulse generation cycle, and $\gamma$ is an adjustment coefficient in a range of 0.4 to 0.6. In response to the peak-to-peak value of the ECAP caused by the pulse generated within the first pulse generation cycle being less than the sensing threshold $ECAP_{th}$, the neural stimulation controller obtains the amplitude of the pulse generated within the next pulse generation cycle according to the preset adjustment coefficient, the amplitude $stim_{th}$ of the pulse corresponding to the sensing threshold $ECAP_{th}$, and the pulse amplitude upper and lower limits in the comfort range, ensuring that the peak-to-peak value of the ECAP caused by the pulse generated within the second pulse generation cycle can be greater than the sensing threshold $ECAP_{th}$.

In some embodiments, in response to the peak-to-peak value of the ECAP sensed within the second pulse generation cycle being still not in the comfort range, similar to the above embodiments, the amplitude of the pulse generated within the next pulse generation cycle (i.e., the third pulse generation cycle) needs to be further adjusted, that is, the amplitude of the pulse generated within the third pulse generation cycle is adjusted to the expected amplitude according to the expected peak-to-peak value. Specifically, as mentioned in the above embodiment, in response to the peak-to-peak value sensed after the pulse is generated within the second pulse generation cycle being still not in the comfort range, the neural stimulation controller obtains the expected peak-to-peak value according to the peak-to-peak value upper and lower limits in the comfort range and an expectation coefficient, obtains an expected amplitude of the pulse according to the expected peak-to-peak value and a transformation coefficient, and uses the expected amplitude as the amplitude of the pulse generated within the third pulse generation cycle. Unlike the above embodiment, in response to the peak-to-peak value of the ECAP sensed within the first pulse generation cycle being less than the sensing threshold $ECAP_{th}$, the neural stimulation controller sets the transformation coefficient to be a ratio of a difference between the peak-to-peak value upper and lower limits in the comfort range to a difference between the pulse amplitude upper and lower limits in the comfort range, and uses this ratio in the calculation of the expected amplitude. That is, the transformation coefficient R in the formula for calculating the expected amplitude is set to be $(ECAP_{up}-ECAP_{lw})/(stim_{up}-stim_{lw})$. This ensures that the expected amplitude is calculated within a range of the linear relationship between the peak-to-peak value of the ECAP and the amplitude of the pulse, so that the calculated expected amplitude is in the comfort range, thereby ensuring the accuracy of pulse adjustment.

In some embodiments, the above neural stimulation device may be applied to spinal cord stimulation or dorsal root ganglion stimulation. The neural stimulation device provided in the embodiments may also be applied to various electrical stimulation scenarios which are not described herein.

In addition, in response to the peak-to-peak value of the ECAP caused by the pulse being small, the neural stimulation controller may also correct the peak-to-peak value of the ECAP using a running average, an assembling average, or the like, avoiding an excessive error in the peak-to-peak value of the ECAP due to various external interferences and further ensuring the effect and accuracy of pulse adjustment. For example, the neural stimulation controller acquires ECAP data at a specific sampling frequency. For the data acquired within a current sampling cycle, the neural stimulation controller does not immediately determine whether it is an extreme value. Instead, the neural stimulation controller uses an average of current data, data from a previous sampling period, and data from a next sampling period as current sampled data, and then determines whether the current sampled data is the extreme value.

In some embodiments, a pulse generation mode of the neural stimulation device in the embodiments is a tonic spiking mode, and every time after instructing the pulse generator to generate a pulse, the neural stimulation controller instructs the ECAP sensor to sense the evoked compound action potential to obtain the peak-to-peak value of the evoked compound action potential, and determines whether the peak-to-peak value is in the comfort range. In some embodiments, the pulse generation mode of the neural stimulation device in the embodiments is a tonic bursting mode, and in response to a last pulse in a group of bursting pulses generated by the pulse generator according to the instruction of the neural stimulation controller, the neural stimulation controller instructs the ECAP sensor to sense the evoked compound action potential to obtain the peak-to-peak value of the evoked compound action potential, and determines whether the peak-to-peak value is in the comfort range. The pulse generation mode of the neural stimulation device includes the tonic spiking mode and the tonic bursting mode. When the pulse generation mode of the neural stimulation device is the tonic spiking mode, for example, the neural stimulation controller instructs the pulse generator to generate a pulse at a pulse generation frequency of 150 Hz or less, e.g., to generate a group of bursting pulses at a generation frequency of 50 Hz. The neural stimulation controller controls the ECAP sensor to sense the evoked compound action potential during instructing the pulse to be generated, so as to obtain the peak-to-peak value of the evoked compound action potential. When the pulse generation mode of the neural stimulation device is the tonic bursting mode, the neural stimulation controller instructs the pulse generator to generate a group of bursting pulses at a certain frequency, for example, to generate a group of bursting pulses at a generation frequency of 400 Hz to 600 Hz. In response to the last pulse in the group of bursting pulses generated by the pulse generator according to the instruction of the neural stimulation controller, the neural stimulation controller instructs the ECAP sensor to sense the evoked compound action potential to obtain the peak-to-peak value of the evoked compound action potential, and determines whether the sensed peak-to-peak value is in the comfort range.

Figure 8:
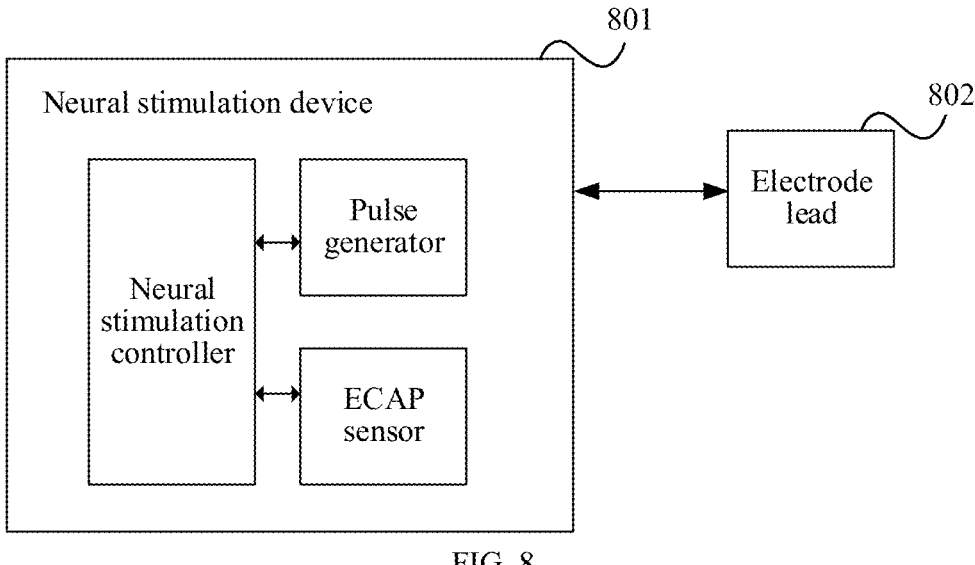
FIG. 8 is a schematic structural diagram of a neural stimulation system according to an embodiment of the present disclosure.

A neural stimulation system provided in another aspect of the embodiments of the present disclosure, as shown in FIG. 8, includes: the neural stimulation device 801 described above and an electrode lead 802 electrically connected to the neural stimulation device. The electrode lead includes a plurality of stimulation electrodes and sensing electrodes. The stimulation electrodes are configured to transmit a stimulation current into a body of a patient, and the sensing electrodes are configured to transmit an evoked compound action potential caused by a stimulation pulse to the ECAP sensor. In this embodiment, a type of the electrodes is not specifically limited, for example, the electrode lead is an electrode lead provided with a ring electrode at distal end. For another example, the electrode lead is an electrode lead provided with a segmented electrode at a distal end. For still another example, the electrode lead is an electrode lead provided with a ring electrode and a segmented electrode at a distal end.

A control method applied at a neural stimulation device including a neural stimulation controller, a pulse generator and an ECAP sensor provided in another aspect of the embodiments of the present disclosure includes the following operations.

After the pulse generator generating a pulse within a first pulse generation cycle, the neural stimulation controller instructs the ECAP sensor to sense an evoked compound action potential, adjusts an amplitude of a pulse generated by the pulse generator within a second pulse generation cycle in response to a peak-to-peak value of the evoked compound action potential that is sensed being not in a comfort range, and adjusts, according to an expected peak-to-peak value, an amplitude of a pulse generated by the pulse generator within a third pulse generation cycle in response to a peak-to-peak value of the evoked compound action potential that is sensed after the pulse is generated by the pulse generator within the second pulse generation cycle being still not in the comfort range. The expected peak-to-peak value is in the comfort range, and the comfort range includes an amplitude dimension of the pulse and a peak-to-peak value dimension of the evoked compound action potential.

It is not difficult to find that this embodiment is a method embodiment corresponding to the device embodiment, and this embodiment may be implemented in cooperation with the device embodiment. The related technical details mentioned in the device embodiment are still effective in this embodiment, and are not repeated here in order to reduce repetition. Accordingly, the related technical details mentioned in this embodiment may also be applied to the device embodiment.

It should be understood by those of ordinary skill in the art that the above embodiments are specific embodiments for implementing the present disclosure, and in practical applications, various changes may be made in form and detail without departing from the spirit and scope of the present disclosure.

What is claimed is:

1. A neural stimulation device, comprising: a pulse generator, an evoked compound action potential (ECAP) sensor, and a neural stimulation controller; wherein the neural stimulation controller is configured to:

instruct the ECAP sensor to sense an evoked compound action potential after a first pulse is generated by the pulse generator within a first pulse generation cycle, adjust an amplitude of a second pulse generated by the pulse generator within a second pulse generation cycle in response to a first peak-to-peak value of the evoked compound action potential that is sensed being not in a comfort range, and adjust, according to an expected peak-to-peak value, an amplitude of a third pulse generated by the pulse generator within a third pulse generation cycle in response to a second peak-to-peak value of the evoked compound action potential that is sensed after the second pulse is generated by the pulse generator within the second pulse generation cycle being still not in the comfort range;

wherein the expected peak-to-peak value is in the comfort range, and the comfort range includes an amplitude dimension of the pulse and a peak-to-peak value dimension of the evoked compound action potential.

2. The neural stimulation device according to claim 1, wherein the neural stimulation controller is further configured to obtain different comfort ranges according to different body postures or different frequencies of pulses.

3. The neural stimulation device according to claim 1, further comprising a body posture sensor; wherein:

the body posture sensor is communicatively connected to the neural stimulation controller and is configured to sense a body posture; and the neural stimulation controller is further configured to obtain the body posture through the body posture sensor to obtain the comfort range corresponding to the body posture.

4. The neural stimulation device according to claim 1, wherein the neural stimulation controller is configured to:

in response to the first peak-to-peak value of the evoked compound action potential that is sensed within the first pulse generation cycle being not in the comfort range, detect a relationship between the first peak-to-peak value and a peak-to-peak value upper limit in the comfort range and a relationship between the first peak-to-peak value and a peak-to-peak value lower limit in the comfort range;

in response to the first peak-to-peak value being greater than the peak-to-peak value upper limit, adjust the amplitude of the second pulse generated within the second pulse generation cycle to a product obtained by multiplying a preset down-adjustment coefficient by an amplitude of the first pulse generated within the first pulse generation cycle; and in response to the first peak-to-peak value being less than the peak-to-peak value lower limit, adjust the amplitude of the second pulse generated within the second pulse generation cycle to a weighted average, obtained according to a preset up-adjustment coefficient, of pulse amplitude upper and lower limits in the comfort range.

5. The neural stimulation device according to claim 4, wherein each of the up-adjustment coefficient and the down-adjustment coefficient is in a range of 0.4 to 0.6.

6. The neural stimulation device according to claim 1, wherein the neural stimulation controller is configured to: in response to the second peak-to-peak value of the evoked compound action potential that is sensed after the second pulse is generated within the second pulse generation cycle being still not in the comfort range, obtain the expected peak-to-peak value according to the peak-to-peak value upper limit and the peak-to-peak value lower limit in the comfort range and an expectation coefficient, obtain an expected amplitude of the pulse according to the expected peak-to-peak value and a transformation coefficient, and use the expected amplitude as the amplitude of the third pulse generated within the third pulse generation cycle.

7. The neural stimulation device according to claim 6, wherein the transformation coefficient is one of a ratio of a difference between the peak-to-peak value upper limit and the peak-to-peak value lower limit in the comfort range to a difference between the pulse amplitude upper and lower limits in the comfort range and a ratio of a difference between the first peak-to-peak value in the first pulse generation cycle and the second peak-to-peak value in the second pulse generation cycle to a difference between an amplitude of the first pulse generated within the first pulse generation cycle and the amplitude of the second pulse generated within the second pulse generation cycle.

8. The neural stimulation device according to claim 6, wherein the expectation coefficient is in a range of 0.4 to 0.6.

9. The neural stimulation device according to claim 6, wherein the neural stimulation controller is configured to calculate the expected amplitude of the pulse according to the following formula:

$$S_t = S_C - \frac{E_C - E_t}{R}$$

wherein $S_t$ is the expected amplitude of the pulse, $S_C$ is the amplitude of the first pulse generated within the first pulse generation cycle, $E_C$ is the first peak-to-peak value of the evoked compound action potential that is sensed within the first pulse generation cycle, $E_t$ is the expected peak-to-peak value, and R is the transformation coefficient.

10. The neural stimulation device according to claim 6, wherein the neural stimulation controller is configured to calculate the expected amplitude of the pulse according to the following formula:

$$S_t = S'_C - \frac{E'_C - E_t}{R}$$

wherein $S_t$ is the expected amplitude of the pulse, $S'_C$ is the amplitude of the second pulse generated within the second pulse generation cycle, $E'_C$ is the second peak-to-peak value of the evoked compound action potential that is sensed within the second pulse generation cycle, $E_t$ is the expected peak-to-peak value, and R is the transformation coefficient.

11. The neural stimulation device according to claim 1, wherein the neural stimulation controller is further configured to: detect whether the first peak-to-peak value of the evoked compound action potential that is sensed within the first pulse generation cycle is less than a sensing threshold, and in response to the first peak-to-peak value of the evoked compound action potential that is sensed within the first pulse generation cycle being less than the sensing threshold, set the amplitude of the second pulse generated within the second pulse generation cycle to an amplitude calculated according to the following formula:

$$stim_2 = stim_1 + stim_{lw} - stim_{ht} + \gamma \times (stim_{up} - stim_{lw})$$

wherein $stim_{up}$ and $stim_{lw}$ are pulse amplitude upper and lower limits in the comfort range, respectively, $stim_{th}$ is an amplitude of a pulse corresponding to the sensing threshold, $stim_1$ is the amplitude of the first pulse within the first pulse generation cycle, and $\gamma$ is an adjustment coefficient in a range of 0.4 to 0.6.

12. The neural stimulation device according to claim 10, wherein the neural stimulation controller is further configured to: in response to the second peak-to-peak value of the evoked compound action potential that is sensed within the second pulse generation cycle being less than the peak-to-peak value lower limit in the comfort range, obtain the expected peak-to-peak value according to the peak-to-peak value upper limit and the peak-to-peak value lower limit in the comfort range and the expectation coefficient, obtain the expected amplitude of the pulse according to the expected peak-to-peak value and a transformation coefficient, and use the expected amplitude as the amplitude of the third pulse generated within the third pulse generation cycle; and wherein the transformation coefficient is a ratio of a difference between the peak-to-peak value upper limit and the peak-to-peak value lower limit in the comfort range to a difference between the pulse amplitude upper and lower limits in the comfort range.

13. The neural stimulation device according to claim 1, wherein the neural stimulation device has a pulse generation mode, and the pulse generation mode includes a tonic bursting mode; and wherein the neural stimulation controller instructs the ECAP sensor to sense the evoked compound action potential in response to a last pulse in a group of bursting pulses generated by the pulse generator according to the instruction of the neural stimulation controller, to obtain a peak-to-peak value of the evoked compound action potential, and determines whether the peak-to-peak value is in the comfort range.

14. The neural stimulation device according to claim 1, wherein the neural stimulation device has a pulse generation mode, and the pulse generation mode includes a tonic spiking mode; and wherein the neural stimulation controller instructs the ECAP sensor to sense the evoked compound action potential every time after instructing the pulse generator to generate the pulse, to obtain a peak-to-peak value of the evoked compound action potential, and determines whether the peak-to-peak value is in the comfort range.

15. The neural stimulation device according to claim 1, wherein the neural stimulation device is applied to spinal cord stimulation or dorsal root ganglion stimulation.

16. A neural stimulation system, comprising a neural stimulation device and an electrode lead electrically connected to the neural stimulation device; wherein the neural stimulation device includes a pulse generator, an evoked compound action potential (ECAP) sensor, and a neural stimulation controller; and wherein the neural stimulation controller is configured to:

instruct the ECAP sensor to sense an evoked compound action potential after a first pulse is generated by the pulse generator within a first pulse generation cycle, adjust an amplitude of a second pulse generated by the pulse generator within a second pulse generation cycle in response to a first peak-to-peak value of the evoked compound action potential that is sensed being not in a comfort range, and adjust, according to an expected peak-to-peak value, an amplitude of a third pulse generated by the pulse generator within a third pulse generation cycle in response to a second peak-to-peak value of the evoked compound action potential that is sensed after the second pulse is generated by the pulse generator within the second pulse generation cycle being still not in the comfort range;

wherein the expected peak-to-peak value is in the comfort range, and the comfort range includes an amplitude dimension of the pulse and a peak-to-peak value dimension of the evoked compound action potential.

17. The neural stimulation system according to claim 16, wherein the neural stimulation controller is further configured to obtain different comfort ranges according to different body postures or different frequencies of pulses.

18. The neural stimulation system according to claim 16, wherein the neural stimulation controller is configured to:

in response to the first peak-to-peak value of the evoked compound action potential that is sensed within the first pulse generation cycle being not in the comfort range, detect a relationship between the first peak-to-peak value and a peak-to-peak value upper limit in the comfort range and a relationship between the first peak-to-peak value and a peak-to-peak value lower limit in the comfort range;

in response to the first peak-to-peak value being greater than the peak-to-peak value upper limit, adjust the amplitude of the second pulse generated within the second pulse generation cycle to a product obtained by multiplying a preset down-adjustment coefficient by an amplitude of the first pulse generated within the first pulse generation cycle; and in response to the first peak-to-peak value being less than the peak-to-peak value lower limit, adjust the amplitude of the second pulse generated within the second pulse generation cycle to a weighted average, obtained according to a preset up-adjustment coefficient, of pulse amplitude upper and lower limits in the comfort range.

19. The neural stimulation system according to claim 16, wherein the neural stimulation controller is configured to:

in response to the second peak-to-peak value of the evoked compound action potential that is sensed after the second pulse is generated within the second pulse generation cycle being still not in the comfort range, obtain the expected peak-to-peak value according to the peak-to-peak value upper limit and the peak-to-peak value lower limit in the comfort range and an expectation coefficient, obtain an expected amplitude of the pulse according to the expected peak-to-peak value and a transformation coefficient, and use the expected amplitude as the amplitude of the third pulse generated within the third pulse generation cycle.

20. A control method, comprising:

applied at a neural stimulation device, wherein the neural stimulation device includes a neural stimulation controller, a pulse generator and an evoked compound action potential (ECAP) sensor, and wherein the neural stimulation controller is configured to:

instruct the ECAP sensor to sense an evoked compound action potential after a first pulse is generated by the pulse generator within a first pulse generation cycle; and adjust an amplitude of a second pulse generated by the pulse generator within a second pulse generation cycle in response to a first peak-to-peak value of the evoked compound action potential that is sensed being not in a comfort range, and adjust, according to an expected peak-to-peak value, an amplitude of a third pulse generated by the pulse generator within a third pulse generation cycle in response to a second peak-to-peak value of the evoked compound action potential that is sensed after the pulse is generated by the pulse generator within the second pulse generation cycle being still not in the comfort range;

wherein the expected peak-to-peak value is in the comfort range, and the comfort range includes an amplitude dimension of the pulse and a peak-to-peak value dimension of the evoked compound action potential.

* * * * *